United States Patent [19]

Washecheck et al.

[11] Patent Number: 4,939,311
[45] Date of Patent: Jul. 3, 1990

[54] CATALYSTS FOR THE OXIDATIVE CONVERSION OF METHANE TO HIGHER HYDROCARBONS

[75] Inventors: Don M. Washecheck; Aileen E. Alvarado-Swaisgood, both of Naperville; Mark P. Kaminsky, Lisle; Mark S. Kleefisch, Plainfield; George A. Huff, Jr., Naperville, all of Ill.

[73] Assignee: Amoco Corporation, Chicago, Ill.

[21] Appl. No.: 233,063

[22] Filed: Aug. 17, 1988

[51] Int. Cl.$^5$ .................................................. C07C 2/00
[52] U.S. Cl. .................................... 585/500; 585/654; 585/656; 585/658; 585/661; 585/700; 585/934
[58] Field of Search ............... 585/500, 520, 530, 654, 585/656, 658, 661, 700, 934

[56] References Cited

U.S. PATENT DOCUMENTS

| | | | |
|---|---|---|---|
| 4,048,245 | 9/1977 | Pollitzer et al. | 260/668 |
| 4,444,984 | 4/1984 | Jones et al. | 585/500 |
| 4,560,821 | 12/1985 | Jones et al. | 585/500 |
| 4,608,449 | 8/1986 | Baerns et al. | 585/500 |
| 4,620,051 | 10/1986 | Kolts et al. | 558/661 X |
| 4,620,052 | 10/1986 | Kolts et al. | 558/661 X |
| 4,634,802 | 1/1987 | Jones et al. | 585/656 |
| 4,665,259 | 5/1987 | Bradzil et al. | 585/500 |
| 4,672,145 | 6/1987 | Kolts et al. | 585/658 |
| 4,780,449 | 10/1988 | Hicks | 502/303 |

Primary Examiner—William R. Dixon, Jr.
Assistant Examiner—James M. Hunter, Jr.
Attorney, Agent, or Firm—Nick C. Kottis; William H. Magidson; Ralph C. Medhurst

[57] ABSTRACT

An oxidative coupling catalyst composition for converting methane to a higher hydrocarbon comprising a mixed oxide of: (a) a Group IIIB metal selected from the grouup consisting of yttrium, scandium and lanthanum; (b) a Group IIA metal selected from the group consisting of barium, calcium and strontium; and (c) a Group IVA metal selected from the group consisting of tin, lead and germanium and approximate ratio of 1:0.5–3:2–4, and an improved process employing same.

10 Claims, No Drawings

CATALYSTS FOR THE OXIDATIVE CONVERSION OF METHANE TO HIGHER HYDROCARBONS

BACKGROUND OF THE INVENTION

This invention relates to oxidative coupling agents or catalysts for the conversion of methane to ethane, ethene and higher hydrocarbons having a greater molecular weight than methane.

In the search for petroleum, large amounts of natural gas are discovered in remote areas where there is no local market for it. The dominant technology now employed for utilizing remote natural gas involves its conversion to syngas, a mixture of hydrogen and carbon monoxide. While syngas processes fulfill the need for an easily transportable liquid that can be converted to several useful products, it is an expensive intermediate. Oxygen is added to the rather inert methane molecule which is advantageous when products such as methanol or acetic acid are desired. In the case of hydrocarbons such as gasoline or diesel fuel, however, syngas processing requires the addition of oxygen, followed by its removal which increases final product cost.

Methane, the predominant component of natural gas, although difficult to activate can be reacted with oxygen or oxygen-containing compounds such as water or carbon dioxide to produce syngas. This mixture is converted to syncrude with Fischer-Tropsch technology and then upgraded to transportation fuels using usual refining methods. Alternatively, syngas can be converted to liquid oxygenates which in turn can be converted to more conventional transportation fuels by catalysts such as certain zeolites.

Because syngas requires high capital investment, is produced in energy wasteful ways as by steam reforming where fuel is burned to supply heat of reforming, and it represents a detour to the production of hydrocarbons, other means of converting methane directly to higher hydrocarbons are needed.

Oxidative coupling has been recognized as a promising approach to the problem of methane conversion although the mechanism of action is not clear. In such processes, methane is contacted with solid materials referred to by various terms including catalysts, promoters, activators or contact materials Methane mixed with oxygen and catalyst is directly converted to ethane, ethylene, higher hydrocarbons and water. Carbon dioxide formation, which is highly favored thermodynamically, is undesirable as both oxygen and carbon are consumed without production of the desired higher value $C_{2+}$ hydrocarbons.

Catalytic mixtures of yttrium-barium-copper oxides are highly active and 100% selective for producing $CO_2$, that is, they are combustion catalysts. In order to obtain the required selectivity to hydrocarbon formation, Group IA metals, particularly lithium and sodium, were used in such catalytic mixtures. Under the conditions used for oxidative coupling, however, migration and loss of the alkali metal normally occurs. In order to avoid complete combustion most methods for oxidative conversion have been carried out in the absence of an oxygen-containing gas, relying on the oxygen theoretically being supplied by the catalyst Thus, the need for highly active, $C_{2+}$ hydrocarbon selective and stable oxidative coupling promoters continues.

Many patents describe processes for converting methane to heavier hydrocarbons in the presence of reducible metal oxide catalysts Most of these patents require or imply the need for a separate stage to re-oxidize the catalyst. These include U.S. Pat. No. 4,444,984 which teaches a reducible oxide of tin as a catalyst; U.S. Pat. No. 4,495,374 disclosing the use of any reducible oxide promoted by an alkaline earth metal; 4,523,049 showing a reducible oxide catalyst promoted by an alkali or alkaline earth, requiring the presence of oxygen during the oxidative coupling reaction U.S. Pat. No. 4,656,155 specifies yttrium in a mixture requiring zirconium and alkali metal. U.S. Pat. No. 4,450,310 claims coupling promoted by alkaline earth oxides in the total absence of molecular oxygen. U.S. Pat. No. 4,482,644 teaches a barium-containing oxygen-deficient catalyst with a perovskite structure European Patent Application No. 198,251 covers a process conducted in the presence of free oxygen using a three component contact material of: (a) an oxide of calcium, strontium or barium, and optionally a material selected from the group consisting of chloride ions, compounds containing chloride ions, tin and compounds containing tin; (b) a sodium or potassium-containing material, and a Group IIA metal or a compound containing one, and optionally a material selected from the group consisting of chloride ions, compounds containing chloride ions, tin and compounds containing tin; (c) a Group IA metal compound, and optionally a material selected from the group consisting of chloride ions, compounds containing chloride ions, tin and compounds containing tin.

U.S. Pat. No. 3,885,020, although disclosing contact materials of the oxidative coupling type, is directed to a method of converting hydrocarbons to $CO_2$ and water for pollution control. The combustion catalysts used consist of four components: (1) zirconium, tin or thorium; (2) an alkaline earth material; (3) a rare earth-type element such as scandium, lanthanum or cesium; and (4) a metal of the first transition series.

Baerns U.S. Pat. No. 4,608,449 relates to a methane conversion process using a suitable metal oxide catalyst, including tin oxide, on an oxide catalyst carrier carried out under temperatures of from 500° C. to 900° C. in the presence of oxygen at specified pressure.

SUMMARY OF THE INVENTION

The present invention provides a three component catalyst for the oxidative conversion of methane to hydrocarbons containing 2 or more carbon atoms. In its broadest aspect, the catalyst composition of this invention comprises a mixed oxide of (a) a Group IIIB metal selected from the group consisting of yttrium, lanthanum and scandium; (b) a Group IIA metal selected from the group consisting of barium, calcium and strontium; and (c) a Group IVA metal selected from the group consisting of tin, lead and germanium; and wherein the cationic species are present in the approximate ratio of 1:0.5–3:2–4. (All periodic table groupings are based on the CAS version of the periodic table).

The preferred catalyst composition comprises a mixed oxide of yttrium, barium and tin in which the cationic species are present in the approximate ratio of 1:2:3, represented by the formula $YBa_2Sn_3O_yC_x$ wherein x is 0 when the cationic species barium is present as the oxide and is not zero when some of the barium species is present as the carbonate. The particularly preferred catalyst of this invention is represented by the formulae $(Y_2O_3)(BaO)_{4-x}(BaCO_3)_x(SnO_2)_6$ wherein x is as defined above.

The catalysts of this invention are extremely stable at oxidative coupling conditions, thereby offering an advantage over the prior art technology.

In another embodiment, the invention provides an improved method for the oxidative coupling of methane to produce hydrocarbons containing 2 or more carbon atoms comprising contacting methane with a catalyst of this invention in the presence of oxygen. Process variable conditions including pressure, temperature, flow rate, feed gas composition and residence time are not critical and may be widely varied within suitable parameters. Conditions should be chosen to cause oxygen conversion to proceed near to, but short of completion in order to protect the catalyst from reduction and degradation. It is preferred to employ temperatures of from about 700°–900° C., low operating pressures, preferably less than 250 psig, and most preferably 1.5 psig.

At temperatures up to 800° C., residence times and relative feed rates are less critical. In operation, feed rates at room temperature and pressure (feed rate/catalyst weight) may be varied from 1000cc/hr/gm-48,000 cc/hr/gm without affecting catalyst performance. At higher temperatures, contact should be short enough to insure near complete oxygen conversion.

The feed preferably comprises pure methane or natural gas with sulfur species removed and oxygen premixed blends in ratios of 2:1 to 20:1 $CH_4$ to $O_2$. The feed may in addition include other species including nitrogen, carbon dioxide, carbon monoxide and water.

The contact solids may be maintained in the contact zone as fixed, moving or fluidizing beds of solids. A fluidized bed operation is preferred.

The catalyst of this invention may be prepared by any suitable method. Generally speaking, dry-mixing followed by calcining is preferred.

DETAILED DESCRIPTION OF PREFERRED EMBODIMENTS

The following examples further illustrate the invention.

EXAMPLE 1

Tin acetate, $Sn(C_2H_3O_2)_2$ (15.0 g, 0.06335 mole, from Alpha Products) was mixed with yttrium carbonate, $Y_2(CO_3)_3\cdot 3H_2O$ (4.12 g, 0.01 mole) and barium hydroxide, $Ba(OH)_2\cdot 8H_2O$ (12.74 g, 0.0404 mole) in a mortar and pestle. The solids were ground into a fine powder. The hygroscopic nature of the solids resulted in the production of a white slurry upon grinding. After the slurry was thoroughly mixed, it was placed in a calcining furnace and heated to 700° C. at a rate of 4° C./min after which it was slowly heated to 800° C. at a rate of 2° C./min where it was held for five hours. The furnace was purged with a flow of air. The solid remained white after calcination. The preparation had a targeted composition of $YBa_2Sn_3O_y$.

EXAMPLE 2

Yttrium nitrate, $Y(NO_3)_3\cdot 6H_2O$ (11.5 g, 0.03 mole) was placed in a quartz crucible and heated to 150° C. in an oven until the solid melted. Barium hydroxide, $Ba(OH)_2\cdot H_2O$ (11.7 g, 0.0618 mole) was added to the melt which was reheated to diffuse the hydroxide salt. After removal from the oven, the slurry solidified and lead nitrate, $Pb(NO_3)_2$ (29.8 g, 0.09 mole) was added and thoroughly mixed. The mixture was heated at a rate of 15° C./min to 600° C. and held there for 5 hours. The furnace was then cooled to 100° C. before the solids were removed. The sample was then calcined to 750° C. for 2 hours, cooled and calcined to 875° C. in air for 5 hours. The solid was black in color. The preparation had a targeted composition of $YBa_2Pb_3O_y$.

EXAMPLE 3

Barium hydroxide, $Ba(OH)_2\cdot H_2O$ (35.1 g, 0.185 mole) was mixed together with lanthanum nitrate, $La(NO_3)_3\cdot 6H_2O$ (39 g, 0.09 mole) and lead nitrate, $Pb(NO_3)_2$ (89.5 g, 0.27 mole). The components were ground to a fine powder before mixing together. The mixture was placed into a quartz crucible and 50 ml of distilled $H_2O$ added thereto, resulting in an orange slurry after the mixture was stirred and gently heated. Additional lanthanum nitrate and lead nitrate were added to the slurry to obtain the correct stoichiometry. After some of the water was evaporated from the slurry by heating overnight at 120° C, the slurry was rehomoginized and heated to 180° C. overnight. The dry material was then placed in a furnace and heated at a rate of 15° C./min to 600° C. and maintained at that temperature for 1 hour. Thereafter, the temperature was raised at a rate 15° C./min to 700° C. The sample was held at 700° C. for 4 hours before cooling. A dark brown solid was obtained having the targeted composition of $LaBa_2Pb_3O_y$.

EXAMPLE 4

The catalyst of Example 1 was placed in a 9 mm internal diameter quartz tube reactor having a 3 mm outside diameter quartz thermowell. A premixed gas blend containing 40% by volume of methane, 4% by volume of oxygen and an inert carrier was employed. Nitrogen was used as an internal standard with an on-line GC mass balance of 100% +2% are obtained with standard deviations of about 0.5% for one run. 40–60 Mesh quartz (Vycor) was used to dilute the 14–40 mesh catalyst loading to obtain a more nearly isothermal bed. A relative feed rate of 1000 standard (room temperature and pressure) cc of feed per hour per gram of catalyst was employed. Product gases were recycled to the front of the reactor and combined with fresh feed at a ratio of about 10:1 recycle to fresh feed. Methane conversion was determined by differences in outlet and inlet molar rates and also by moles of products formed. Oxygen was nearly completely consumed (98%+) for temperatures of from 600° to 750° C. $C_2+$ selectivity improved with increasing temperatures and reached about 50% at 750° C. The only other major carbon-containing product was $CO_2$.

EXAMPLE 5

The catalyst of Example 1 was retested following the method of Example 4 at a fixed temperature of 750° C. and relative feed rates (feed rate/catalyst weight) of about 5, 10 and 15 times that used in Example 4. Even at these increased feed rates, oxygen consumption remained high (92-98%). $C_2+$ selectivity was relatively insensitive to these variations.

EXAMPLE 6

The catalyst of Example 3 was tested at the high relative flow rates employed in Example 5 (i.e. 15,000 cc/hour-gm). Selectivity was comparable to that of the catalyst of Example 1.

EXAMPLE 7

The catalyst of Example 2 was also tested at the high relative flow rates employed in Example 5. Performance was comparable, but not identical, to that of the catalyst of Example 3. This catalyst had a lower oxygen conversion rate at temperatures below 750° C. At 750° C. and at 600° C. after being at 700° C., the oxygen conversion rates were nearly identical, as were the selectivities.

EXAMPLE 8

The catalyst of Example 1 was tested at higher feed rates and temperatures, without recycling. The feed composition was also varied. The reaction conditions are summarized below.

| $CH_4:O_2$ | W/F(cc/gm-hr) | Max Temp, °C. |
|---|---|---|
| 2:1 | 24,000 | 750 |
| 10:1 | 42,000 | 850 |
| 10:1 | 48,000 | 875 |

The first run showed little catalyst performance change over a 20 hour testing cycle. The feed was changed to a higher $CH_4:O_2$ ratio for runs 2 and 3. At 850° C. in run 2, selectivity to $C_2+$ reached about 68% with $CO_2$ making up most of the balance. Even at the high relative feed rates, near full oxygen conversion was observed. In run 3, both maximum temperature and the feed rate were increased. The catalyst began to change significantly at 875°. When the temperature was lowered to 850° C. after having been at 875° C., the catalyst showed a significant loss in $C_2+$ sensitivity.

Although embodiments of this invention have been shown and described, it is to be understood that various modifications and substitutions, as well as rearrangement and combination of parts, components, equipment and/or process steps can be made by those skilled in the art without departing from the novel spirit and scope of this invention.

What is claimed is:

1. An improved method for converting methane to a higher hydrocarbon comprising the steps of: contacting a gas comprising methane with an oxidative coupling catalyst comprising a mixed oxide of: (a) a Group IIIB metal cationic species selected from the group consisting of yttrium, lanthanum, and scandium; (b) a Group IIA metal cationic species selected from the group consisting of barium, calcium and strontium; and (c) a Group IVA metal cationic species selected from the group consisting of tin, lead and germanium and wherein the Group IIIB metal, Group IIA metal and Group IVA metal are present in the approximate atomic ratio of 1:0.5-3:2-4-1, respectively, in the presence of oxygen.

2. The process of claim 1 wherein methane and oxygen are contacted with said catalyst at a temperature of from 700°-900° C.

3. The process of claim 1 wherein the Group IIIB, metal, Group IIA metal and Group IVA metal of said catalyst composition are present in an atomic ratio of 1:2:3, respectively.

4. The process of claim 2 wherein the Group IIIB metal, Group IIA metal and Group IVA metal of said catalyst composition are present in an atomic ratio of 1:2:3, respectively.

5. The process of claim 1 wherein said catalyst is a mixed oxide of yttrium, barium and tin.

6. The process of claim 5 wherein the yttrium, barium and tin are present in an atomic ratio of 1:2:3, respectively.

7. The process of claim 1 wherein the catalyst composition is represented by the empirical formula $YBa_2Sn_3O_y$ wherein y has a value in the range of 6.5 to 11.5.

8. The process of claim 1 wherein the catalyst composition additionally comprises at least a portion of the barium cationic species present in the form of a carbonate, and wherein the catalyst composition is represented by the empirical formula $YBa_2Sn_3C_xO_y$ wherein x has a value greater than zero and up to and including 2 and y has a value in the range of 6.5 to 13.5.

9. The process of claim 1 wherein the catalyst composition additionally comprises at least a portion of the barium cationic species present in the form of a carbonate, and wherein the catalyst composition is represented by the formula $(Y_2O_3)(BaO)_{4-x}(BaCO_3)_x(SnO_2)_6$ wherein x has a value greater than zero and up to and including 4.

10. The process of claim 1 wherein the catalyst composition is represented by the formula $(Y_2O_3)(BaO)_4(SnO_2)_6$.

* * * * *

UNITED STATES PATENT AND TRADEMARK OFFICE
CERTIFICATE OF CORRECTION

PATENT NO. : 4,939,311

DATED : July 3, 1990

INVENTOR(S) : Don M. Washecheck, et al.

Page 1 of 2

It is certified that error appears in the above-identified patent and that said Letters Patent is hereby corrected as shown below:

| Col. | Line | | |
|---|---|---|---|
| 2 | Abstract 4 | "grouup" should be --group-- | |
| 2 | Abstract 8 | "and approximate" should be --and wherein the cationic species are present in the approximate-- | |
| 1 | 45 | "materials Methane" should be --materials. Methane-- | |
| 1 | 63 | "catalyst Thus" should be --catalyst. Thus-- | |
| 1 | 68 | "catalyst Most" should be --catalyst. Most-- | |
| 2 | 8 | "reaction U.S." should be --reaction. U.S.-- | |
| 2 | 14 | "structure European" should be --structure. European-- | |

UNITED STATES PATENT AND TRADEMARK OFFICE
CERTIFICATE OF CORRECTION

PATENT NO. : 4,939,311

DATED : July 3, 1990

INVENTOR(S) : Don M. Washecheck, et al.

It is certified that error appears in the above-identified patent and that said Letters Patent is hereby corrected as shown below:

| Col. | Line | |
|---|---|---|
| 2 | 49 | "of (a)" should be --of: (a)-- |
| 3 | 25 | "performance At" should be --performance. At-- |
| 3 | 29 | "20:1 $CH_4$" should be --20:1, $CH_4$-- |
| 4 | 20 | "rehomoginized" should be --rehomogenized-- |
| 6 | 8 | "3:2-4-1," should be --3:2-4,-- |

Signed and Sealed this

Twenty-fourth Day of September, 1991

Attest:

HARRY F. MANBECK, JR.

Attesting Officer

Commissioner of Patents and Trademarks